United States Patent [19] [11] 4,045,319
Deportes et al. [45] Aug. 30, 1977

[54] ELECTROCHEMICAL GAGE FOR MEASURING PARTIAL PRESSURES OF OXYGEN

[75] Inventors: Charles Henri Deportes, Brignoud; Marc Patrice Sylvain Henault, Gieres; Francis Tasset, Fontaine; Gerard Raymond Robert Vitter, Saint-Martin-D'Heres, all of France

[73] Assignee: Agence Nationale de Valorisation de la Recherche (ANVAR), Neilly-sur-Seine, France

[21] Appl. No.: 504,630

[22] Filed: Sept. 9, 1974

[30] Foreign Application Priority Data
Sept. 11, 1973 France .................. 73.32671

[51] Int. Cl.² .................. G01N 27/46
[52] U.S. Cl. .................. 204/195 S
[58] Field of Search .................. 204/195 S, 195 F; 136/86 F, 120 FC

[56] References Cited

U.S. PATENT DOCUMENTS

| | | | |
|---|---|---|---|
| 3,400,054 | 9/1968 | Ruka et al. | 204/195 S |
| 3,429,749 | 2/1969 | Baukal | 136/86 F |
| 3,462,353 | 8/1969 | Every et al. | 204/195 F |
| 3,630,874 | 12/1971 | Olette et al. | 204/195 S |
| 3,706,602 | 12/1972 | Miller | 136/120 FC |
| 3,719,576 | 3/1973 | Macur | 204/195 P |
| 3,723,279 | 3/1973 | Fruehan et al. | 204/195 S |
| 3,767,469 | 10/1973 | Flais et al. | 204/195 S |

Primary Examiner—T. Tung
Attorney, Agent, or Firm—Weiser, Stapler & Spivak

[57] ABSTRACT

An electrochemical gage for measuring partial pressures of oxygen. The gage is preferably in miniaturised form and uses an internal reference or standard of palladium: palladium oxide. The internal reference is disposed in a compartment defined by walls of solid electrolyte.

23 Claims, 6 Drawing Figures

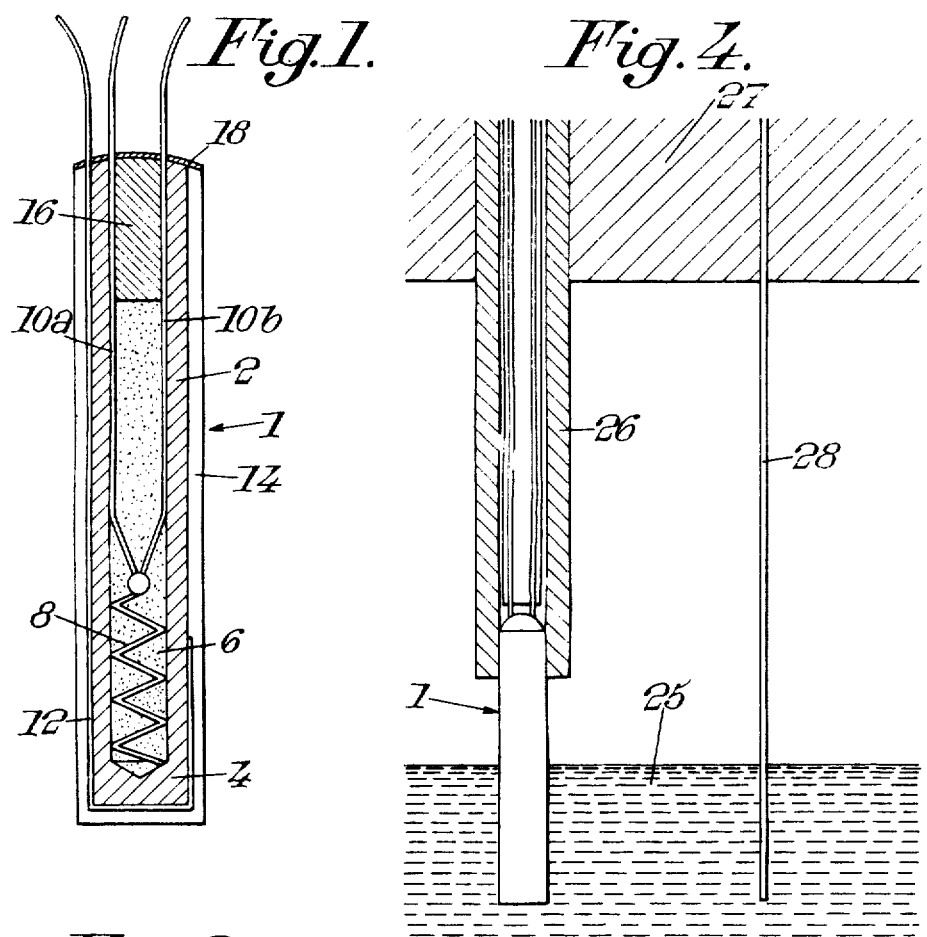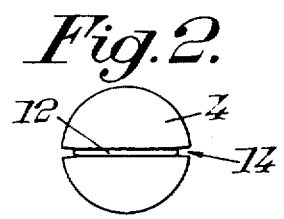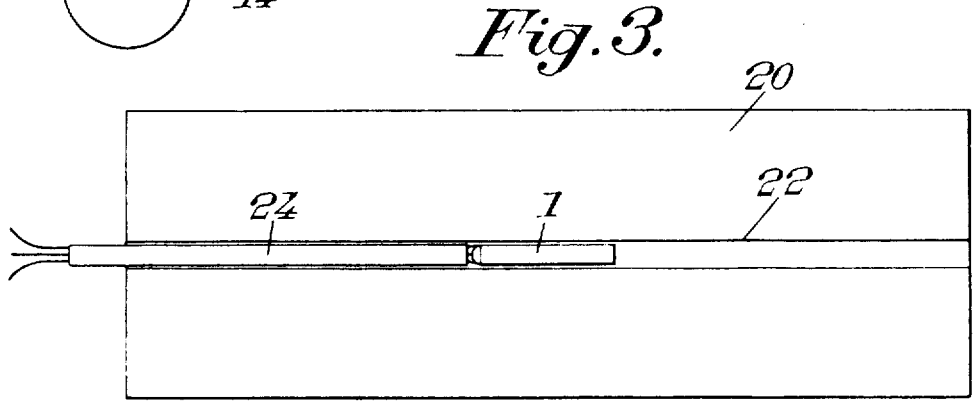

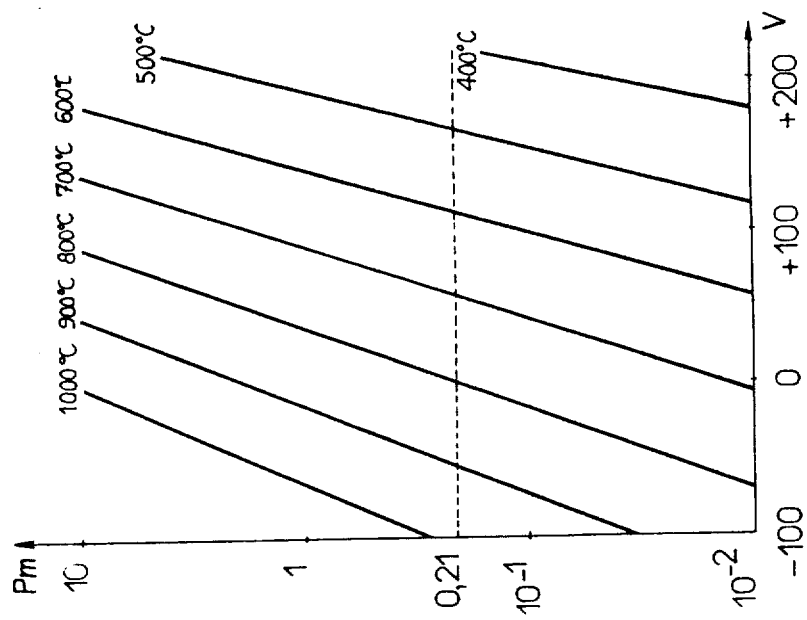
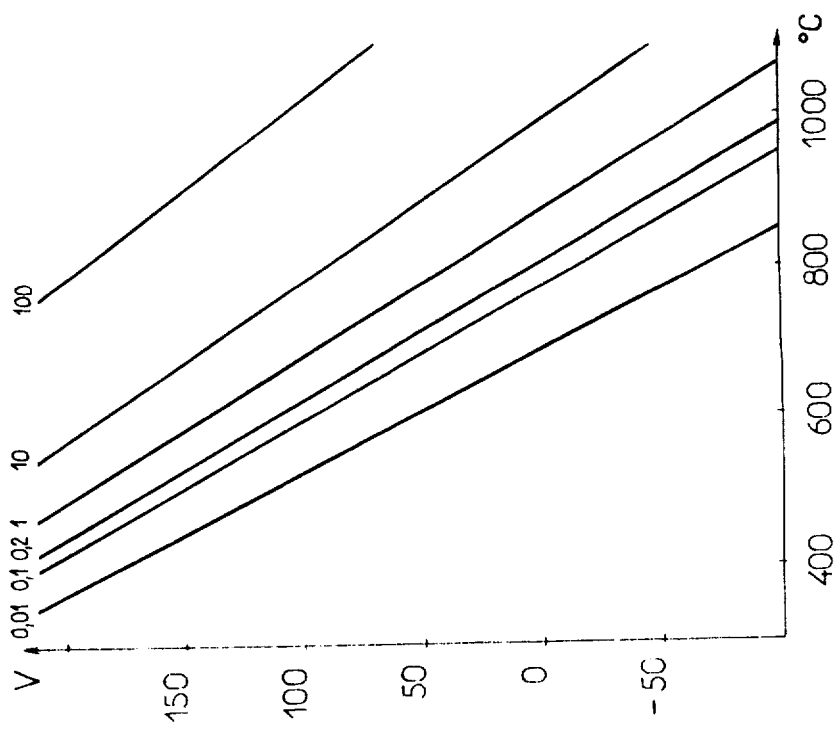

ELECTROCHEMICAL GAGE FOR MEASURING PARTIAL PRESSURES OF OXYGEN

FIELD OF THE INVENTION

This invention relates to an electrochemical oxygen gage with a solid oxide electrolyte and a solid internal reference: this oxygen gage is constructed preferably in miniaturised form and is capable of functioning under any pressure, high pressures included.

THE PRIOR ART

It will be remembered that an oxygen gage with solid oxide electrolyte can be assimilated to a galvanic cell of the type:

| "Reference" compartment | $\left\{ \begin{array}{c} M, O_2(P_{ref}) \\ \text{reference} \\ \text{electrode} \end{array} \right.$ | Solid oxide electrolyte | $\left. \begin{array}{c} M', O_2(P_m) \\ \text{measuring} \\ \text{electrode} \end{array} \right\}$ | "measuring" compartment |
|---|---|---|---|---| in which:

M and M' are unoxidizable electronic conductors, for example consisting of one of the noble metals, the solid oxide electrolyte is an oxide ceramic or possibly a vitreous phase with pure ionic conduction, for example a solid solution of oxides defective in oxide ions and with a fluorite-type structure, such as that described by D. Yuan and F. A. Kroeger in J. Electrochem. Soc. 118, 841 (1971).

The "reference" compartment uses a chemical system consisting of either a gaseous mixture (pure oxygen, oxygen-gas mixture, $CO-CO_2$, $H_2O$), or a metal-oxide mixture, for example $Fe-Fe_{1-x}O$, $Ni-NiO$, etc. or even a mixture of two oxides of the same metal, for example $(CoO-Co_3O_4$.

The use, particularly for measuring partial pressures of oxygen, for example in specific atmospheres or in molten metallic phases, etc., of electrochemical oxygen gages in which the chemical system used to establish the reference pressure $P_{ref}$ consists of a gaseous mixture of the type described above, is very awkward. In order to obtain accurate measurements, it is particularly required that in every case circulation must be ensured of a gas whose oxygen partial pressure has been exactly predetermined in the reference compartment.

The use of gages in which the reference pressure is established by a mixture or couple of the form metal:oxide of the same metal, or oxide:oxide, or similar redox couple, therefore seems a priori much more satisfactory. This mixture which will be referred to from now as "internal reference" enables the partial pressure of oxygen to be established with reference to a fixed value, when the temperature is constant and when heterogeneous equilibrium is reached. It is then possible, once the temperature is maintained constant and heterogeneous equilibrium established, to obtain accurate measurements, while dispensing with circulation of gas in the reference compartment and consequently with all the difficulties posed by keeping the partial pressure of oxygen in this gas constant.

There have already been described a great number of redox couples of the above-mentioned type which, when placed in a galvanic cell of the kind mentioned above, would be capable of engendering a partial pressure of oxygen from the moment when heterogeneous equilibrium is reached. A number of gages utilising this principle have also already been described. However, known gages have various drawbacks which considerably limit their possibilities of use.

It will in fact be noted that, in the redox couples whose use in gages has already been suggested, the partial pressures of oxygen in the internal reference which are obtained at equilibrium are very weak, and these gages can function only at very high temperatures, generally above 800° – 1000° C. Furthermore, bringing the internal reference and the gas to be studied to thermodynamic equilibrium at the chosen operational temperature takes an extremely long time, so that obtaining a measurement with these gages requires a prolonged period of time; moreover, that results are often distorted when the temperature is subject to fluctuations, since these cannot be compensated for each time by an immediate return to equilibrium of the thermodynamic system under consideration.

The extreme weakness of the partial pressures of oxygen in the reference compartment of known gages also means that the slightest deficiency in the permeability of the electrolyte, the smallest leak, renders the gage completely useless.

SUMMARY OF THE INVENTION

This invention therefore aims at remedying these defects, and in particular at producing an electrochemical oxygen gage with an internal reference, capable of being used in relatively low temperatures, of being rapidly brought to a state of equilibrium at the requisite operational temperature and, if this temperature should vary, of being rapidly corrected; and which, moreover, offers high mechanical resistance.

In accordance with this invention a palladium-palladium oxide redox couple is used as the internal reference of an electrochemical gage of the type in question.

In the preferred oxygen gage according to this invention the internal reference compartment is bounded at least in part by the solid electrolyte, this compartment contains a mass of palladium, of palladium oxide, or of a mixture of palladium and palladium oxide, at least one electronic conductor (hereafter referred to as "interior electronic conductor") is in contact both with the electrolyte within this compartment and with the contents of the compartment, and this compartment is hermetically closed, preferably sealed at the point where the electronic conductor leaves this compartment, so as to prevent any direct contact between the contents and the outside atmosphere.

The use of such a gage naturally implies the presence of a second electronic conductor in electrical contact (hereafter called "exterior electronic conductor") with the solid electrolyte in the measuring compartment or its equivalent, especially when the gage is used for determining the partial pressure of oxygen in a specific atmosphere, of a bath, for example of molten metal, etc.

In one recommended method of construction of the gage according to the invention, the compartment containing the internal reference takes the form of a tube or sheath elements, formed by the solid oxide electrolyte itself.

The use of a palladium-palladium oxide couple in electrochemical gages of this type enables all the defects mentioned above to be remedied.

It has in fact been discovered that the kinetics of the bringing to equilibrium of this couple in the conditions described above is very rapid; the fact that the partial pressures of the reference oxygen of the couple according to the invention are considerably more important than those of other couples used hitherto, and this at much lower temperatures, is also shown to be particularly favourable to the efficient functioning of the gages. Purely as an indication, these partial pressures can vary between values of the order of $10^{-3}$ and the order of the atmosphere depending on the operational temperature. Gages so constituted are both more accurate and, especially where very high partial pressures of the reference oxygen are concerned, less sensitive to minor permeability deficiencies of the electrolyte.

Gages so constituted function perfectly at temperatures below 800° C, temperatures which are low in the technical field under consideration. The oxygen exchange reaction between the palladium and the palladium oxide of the internal reference is still sufficiently rapid and reversible at 400° C.

Another advantage deriving from use of the Pd-PdO couple lies in the possible regeneration, under relatively low recharge potential, of the internal reference by electrolytic reduction of the oxide or electrolytic oxidation of the reference metal, after operation of the minigage has caused the transformation of the palladium-palladium oxide mixture into one or other of its pure constituents, or at least into proportions which are no longer compatible with correct functioning of the minigage.

Electrochemical gages according to the invention may easily be miniaturized. Among the essential advantages of miniaturization must be reckoned the homogeneity of temperature in the masses of the internal reference and the electrolyte sheath respectively, thus eliminating risks of error due to temperature gradients, which in larger gages can often be avoided only with great difficulty. This advantage becomes more appreciable in that in the neighbourhood of 500° C, a rise in temperature of 20° C results in the effective doubling of the reference pressure.

Miniaturization is also accompanied by an increase in the mechanical resistance of these gages, so that they may be used for measuring the relative oxygen content in atmospheres maintained at high pressures. These minigages are also easily utilised in cold enclosures. They are then used in conjunction with small furnaces which, given that minigages according to the invention may be constructed in very small sizes, may be of inconsiderable bulk and consume hardly any electric power.

BRIEF DESCRIPTION OF DRAWINGS

Other characteristics of the invention will emerge in the course of the description which follows of preferred methods of construction of electrochemical gages according to the invention and the results which may be obtained with them, especially with reference to the figures, in which:

FIG. 1 shows an axial section across a gage constructed according to one of the preferred methods for the invention, FIG. 2 is the same gage seen from above, FIG. 3 is a diagram of such a minigage in conjunction with a furnace which enables it to be brought to the desired temperature, FIG. 4 is a diagram of a variant of the gage in FIG. 1 and a method of utilising this gage, particularly for determining the partial pressure of oxygen in a liquid bath, for example in a molten metal, FIG. 5 shows the curves representing variations of the emf of such a gage as a function of the temperature, for various constant values of exterior partial pressures of oxygen, FIG. 6 shows the curves representing variations in the emf of such a gage as functions of the exterior partial pressure of oxygen for various temperature values.

DETAILED DESCRIPTION OF DRAWINGS

The "minigage" shown in FIG. 1, and generally designated as 1, comprises a sheath 2, closed at its lower end 4 and made of a material suitable for constituting the solid electrolyte of such a minigage. This sheath provides a compartment 6 containing a mixture of palladium and palladium oxide which acts as internal reference. A lower electric conductor is maintained in contact with both the solid electrolyte and with the internal reference mixture, this conductor communicating with the exterior by means of the limbs 10a and 10b of a thermocouple. An exterior conductor 12 is maintained in contact with the electrolyte, in particular in the grooves 14 formed in the exterior surfaces and the bottom of the sheath 2. A stopper 16, preferably of the same material as the sheath 2, and a seal 18, ensures the tight seal of the compartment containing the internal reference around the conductors 10a, 10b and 12 and, consequently, prevents any exterior contact between this internal reference and the atmosphere.

In the construction shown in FIG. 1, the sensitive part of the thermocouple combined with the minigage is lodged in the interior compartment 6 of the gage. It may equally well be mounted on the exterior of the electrolyte. In particular, its two opposite limbs may be mounted in the two lateral grooves formed in the exterior surface of the sheath formed by the electrolyte, these limbs being then soldered together immediately under the lower part 4 of the gage.

In the construction which has just been described, the solid electrolyte may be any conventional solid oxide electrolyte for constructing oxygen gages e.g., a solid function of zirconia and yttrium oxide, stabilized zirconia, a solid solution of thoriabased oxides, etc. It must be made sufficiently tight e.g., by sintering or by cutting a monocrystal and its electronic conduction must be sufficiently weak under operational conditions.

The seal 18 should be constructed of a material which will remain sufficiently resistant to the operational temperature and sufficiently impermeable to oxygen. An enamel, particularly of Pyrex glass, is recommended.

The palladium-palladium oxide mixture is introduced into or formed in the compartment 6 in various ways:

1. by direct introduction into the gage before sealing of a carefully-blended mixture of powdered palladium and palladium oxide;

2. by introduction of powdered palladium only, then, after sealing, by partial oxidation by continuous passage of current, the interior electrode 8 being taken as an anode and the exterior electrode 12 kept in air;

3. by introduction into the reference compartment of palladium oxide and, after sealing, by partial reduction of the oxide by electrolysis at a sufficiently high temperature (of the order of 1,000° C), the interior electrode 8 being taken as a cathode.

It will be noted that this last method of proceeding may possibly be utilized for regeneration of the reference electrode of the minigage if, after prolonged operation at high oxygen pressure, the palladium has been completely transformed into oxide by the oxygen penetrating the reference compartment through leaks in the seal, permeation of the electrolyte or accidental "short-circuit" between the leads to the electrodes.

The electronic conductors or leads may be made of metal or alloy, unoxidisable under operational conditions, for example platinum alloyed with rhodium, or silver.

In order to improve contact with the electrodes, the electrolyte may be covered with a layer of unoxidizable material, electronically conducting or having mixed conduction properties, such as a precious metal or a semi-conducting oxide stable under operating conditions (for example $V_2O_5$, $RuO_2$, $NiPr_2O_4$, etc.).

In this way a minigage has been constructed in accordance with FIGS. 1 and 2, using an electrolyte sheath of zirconia 12mm long and with an exterior diameter of 2mm. The useful volume for the internal reference of such a gage is of the order of 10mm$^3$. The limbs 10a and 10b of the thermocouple are respectively of platinum and of platinum alloyed with rhodium. The exterior conductor 12 is also of platinum. Even smaller gages may be constructed with, for example, an exterior diameter of the order of 1mm.

A minigage so constructed may be used directly inside a heated enclosure containing the gaseous mixture of which it is desired to measure the oxygen partial pressure.

The very small size of such a minigage allows it to be used in small isothermic enclosures.

It is also possible to use it inside a large non-isothermic enclosure, if this includes a region where the temperature gradient is not too high. In particular, this makes it possible to measure the oxygen partial pressure in an enclosure where the maximum temperature is higher than the limit of temperature at which the minigage will operate.

Such a minigage is also capable of operating in cold enclosures. It must then be used in conjunction with a small furnace which, in view of the small size of the minigage, is not cumbersome and consumes very little electrical power. Such a furnace 20 is shown diagrammatically in FIG. 3, the gage 1 being then placed in the central canal 22 of this furnace. The conductors leading from the gage are then protected by an isolating sheath 24. The same minigage may also be used to measure the partial pressure of oxygen in a liquid bath, in particular a mass of molten metal 25 (FIG. 4). It is then equally necessary to protect the conductors leading from the gage. For this particular application, it will be useful to employ an apparatus of the kind shown in FIG. 4 or similar, the gage being then held by its upper part in a tube of isolating material 26 which forms an integral piece with a part 27 and in particular with the cover of the tank containing the bath: this tube thus protects the leads and thermocouple conductors from contact with the bath 25 and any corrosive vapours emanating from it.

For such an application, it is advisable to construct the exterior conductor 12 from materials which do not react with the liquid metallic phase and which do not dissolve in it. The external conductor 12 may moreover be eliminated and replaced with a separate lead 28 immersed in the bath.

Such minigages are capable of quite remarkable performances, as attested by the following trial results.

Various minigages have been constructed on the principles of the diagrams in the figures. They operate in a temperature range of 400° – 1,000° C. One of them, allowed to function continuously in air at 450° C (potential 183 mV), is still functioning perfectly after a period of six months. During the whole of that period its potential has remained constant within fluctuations of plus or minus 1 mV approximately, due to variations in the barometric pressure which cause corresponding variations in the partial pressure of oxygen in the air.

A minigage of this type mounted in a small furnace was tested (up to 100 bars) in a high-pressure shell with helium-oxygen and argon-oxygen mixtures. The results show that the minigage resists pressures of a least 100 bars at temperatures between 0 and 700° C and that its potential at a given temperature is independent of the partial pressure of helium or argon and depends solely on the partial pressure of oxygen.

Conversely, a minigage according to the invention was submitted to a pressure of 300 bars of argon at 400° C for a period of an hour. After decompression, this gage continued to function normally.

A minigage according to the invention was brought several times from ordinary temperature to 500° C in about a minute. No deterioration due to thermal shock could be observed. Equilibrium tension is reached, when the gas under analysis is air, five seconds after stabilization of the temperature.

The lines in FIG. 5 represent variations of the emf (V) — expressed in millivolts on the ordinate axis — as a function of the temperature — expressed in ° C on the abscissa axis — for various values, shown on each of the lines at the top of FIG. 5, of the partial pressure $P_m$ of oxygen in a test gas in which the minigage being tested was immersed. These variations are appreciably linear in the 400° – 800° C range.

The lines in FIG. 6 give the value of the pressure $P_m$ — expressed in atmospheres on the ordinate axis (logarithmic units) — as a function of the emf — expressed in millivolts on the abscissa axis — at various operational temperatures between 500° and 1,000° C. It follows naturally that gages according to this invention may equally well be used at very high temperatures, providing that the solid electrolyte and the electronic conductors are made of materials resistant to such conditions, such as are well known to specialists.

Consequently minigages may be constructed which are exceptionally sensitive, accurate, solid and characterized by a particularly low cost price.

As will be obvious and indeed has already been demonstrated, this invention is in no way limited to the construction methods especially considered; on the contrary, it is open to any number of variations.

We claim:

1. In an electrochemical gage for measuring partial pressures of oxygen, said gage comprising a solid electrolyte and an internal reference, the improvement whereby the internal reference consists essentially of a palladium:palladium oxide redox couple.

2. An electrochemical oxygen gage, said gage including an internal reference compartment with a hermetic seal, said compartment being substantially filled with an internal reference consisting of solid material selected from the class consisting of palladium, palladium oxide and mixtures thereof, said compartment being defined at least in part by a solid electrolyte, and at least one electronic conductor leading into said compartment and electronically connected within said compartment both with the reference material and said electrolyte.

3. A gage according to claim 2 wherein said compartment is sealed at the point where said conductor enters.

4. A gage according to claim 2 wherein said compartment is in the shape of a sheath which is closed at one end and which is formed of said solid electrolyte.

5. A gage according to claim 4 wherein said sheath is sealed around said conductor at the end of the sheath opposite to the said one end.

6. A gage according to claim 2 including a thermocouple mounted inside said compartment.

7. A gage according to claim 6 wherein said thermocouple has a pair of limbs at least one of which constitutes at least a part of said conductor.

8. A gage according to claim 6 wherein said thermocouple has a pair of limbs and said electronic conductor is constituted by one of said limbs, the other limb being in electronic contact with the interior surface of the electrolyte.

9. A gage according to claim 2 including an exterior electronic conductor attached in electronic contact with the exterior surface of said electrolyte.

10. The gage of claim 9, wherein the exterior conductor is positioned in a groove in the exterior surface of the electrolyte.

11. The gage of claim 9, wherein the one electronic conductor has a generally serpentine shape and touches the interior surface of the compartment at the peaks.

12. The gage of claim 11, wherein alternate peaks of the conductor touch opposite surfaces of the compartment.

13. The gage of claim 2, wherein the compartment is not more than about 12 mm long and has an exterior diameter of not more than about 2 mm.

14. The gage of claim 13 having an internal reference compartment volume of no more than about 10 mm³.

15. The gage of claim 13 having an external diameter of the order of 1 mm.

16. The gage of claim 2, in combination with means for supplying current to the gage to produce transfer of oxygen through the solid electrolyte in a direction to regenerate the reference material within the compartment.

17. An oxygen gage comprising a sheath which is closed at one end and which is formed of solid electrolyte, said sheath having interior and exterior surfaces,
an internal reference material within said sheath, said material consisting essentially of palladium and palladium oxide in intimate association,
a thermocouple including a pair of leads within said internal reference material, and making electrical contact with said reference material and said interior surface of said sheath, at least one of said leads constituting an internal electrode,
said sheath being hermetically sealed around said leads and
an exterior electrode attached in electrically conductive contact with the exterior surface of said electrolyte.

18. A system for measuring partial oxygen pressures in cold enclosures, said system comprising a gage which includes a solid electrolyte and an internal reference consisting essentially of a palladium: palladium oxide redox couple, and means for raising the temperature of said gage to operating levels.

19. A system for measuring partial oxygen pressure in a liquid bath, said system comprising a gage for insertion in said bath including a solid electrolyte and an internal reference consisting essentially of a palladium: palladium oxide redox couple, and conductor means external of said gage for contacting said bath.

20. An electrochemical gage for measuring the partial pressure of oxygen in a medium, which comprises:
a solid oxide electrolyte having ionic conduction and forming at least part of the walls of a compartment;
a chemical system within said compartment effective for providing a reference pressure of oxygen at a determined temperature;
an inner electronic conductor electrode in contact with said solid electrolyte within said compartment,
an outer electronic conductor electrode outside said compartment for providing electric contact to said outside, both said electrochemical gage and said outer electronic conductor being adapted to be brought in contact at an operative temperature with the medium containing the oxygen under partial pressure to be measured; and
said chemical system consisting essentially of a palladium: palladium oxide redox couple.

21. An electrochemical gage according to claim 20, wherein said compartment has a hermetic seal and wherein said inner electronic conductor electrode is formed of a conductor in electronic contact both with the chemical system and said solid electrolyte, said inner electronic conductor electrode passing through the seal of said compartment.

22. An electrochemical gage according to claim 15 wherein said chemical system substantially fills the interior of said compartment.

23. An electrochemical gage for measuring the partial pressure of oxygen in a medium, said gage comprising:
a solid oxide electrolyte having ionic conduction and forming at least part of the walls of a compartment,
a solid chemical system substantially filling said compartment, said system being responsive to the application of predetermined electrical energy to form a redox-mixture of a metal and an oxide of the same metal providing a reference pressure of oxygen at a determined temperature,
an inner electronic conductor electrode in contact with said solid electrolyte within said compartment,
an outer electronic conductor electrode outside said compartment for providing electric contact to said outside, both said electrochemical gage and said outer electronic conductor being adapted to be brought in contact at an operative temperature with the medium containing the oxygen under partial pressure to be measured, and
said solid chemical system being formed of palladium, palladium oxide, or a mixture thereof.

* * * * *